(12) United States Patent
Niwa et al.

(10) Patent No.: US 7,648,458 B2
(45) Date of Patent: Jan. 19, 2010

(54) INSERTION SHAPE DETECTING PROBE

(75) Inventors: Hiroshi Niwa, Tokyo (JP); Chieko Aizawa, Tokyo (JP)

(73) Assignee: Olympus Corporation, Tokyo (JP)

( * ) Notice: Subject to any disclaimer, the term of this patent is extended or adjusted under 35 U.S.C. 154(b) by 652 days.

(21) Appl. No.: 11/545,679

(22) Filed: Oct. 10, 2006

(65) Prior Publication Data

US 2007/0043260 A1 Feb. 22, 2007

Related U.S. Application Data

(63) Continuation of application No. PCT/JP2005/006964, filed on Apr. 8, 2005.

(30) Foreign Application Priority Data

Apr. 9, 2004 (JP) .............................. 2004-115848

(51) Int. Cl.
*A61B 1/00* (2006.01)
*A61B 5/05* (2006.01)
(52) U.S. Cl. ...................... 600/130; 600/117; 600/424
(58) Field of Classification Search ................. 600/117, 600/130, 145, 424
See application file for complete search history.

(56) References Cited

U.S. PATENT DOCUMENTS 5,997,473 A * 12/1999 Taniguchi et al. ........... 600/117
6,511,417 B1 * 1/2003 Taniguchi et al. ........... 600/117
6,745,065 B2 * 6/2004 Niwa et al. .................. 600/424
6,773,393 B1 * 8/2004 Taniguchi et al. ........... 600/117
6,773,394 B2 * 8/2004 Taniguchi et al. ........... 600/117
6,890,294 B2 * 5/2005 Niwa et al. .................. 600/106
2003/0028096 A1 2/2003 Niwa et al.
2004/0116775 A1 * 6/2004 Taniguchi et al. ........... 600/117

FOREIGN PATENT DOCUMENTS

JP 2003-47586 2/2003

* cited by examiner

*Primary Examiner*—Linda C Dvorak
*Assistant Examiner*—Alireza Nia
(74) *Attorney, Agent, or Firm*—Scully, Scott, Murphy & Presser, P.C.

(57) ABSTRACT

An insertion shape detecting probe includes shape detecting elements for generating or detecting magnetic field or magnetic; signal lines connected to the shape detecting elements; supporting members that support the shape detecting elements; inner sheaths into which the signal lines and the supporting members are inserted; and an outer sheath into which the inner sheaths, the shape detecting elements, and at least one portion of the supporting members are inserted. The inner sheaths are each formed from a multiple-lumen tube that has a first lumen formed at a substantially central portion of each inner sheath and second lumens formed around an exterior periphery portion of the first lumen, and the supporting members are elongated wire rods one portion of which is arranged along exterior peripheries of the shape detecting elements in an axial direction and other portion runs through the second lumens.

13 Claims, 9 Drawing Sheets

INSERTION SHAPE DETECTING PROBE

CROSS-REFERENCE TO RELATED APPLICATIONS

This application is a continuation of PCT international application Ser. No. PCT/JP2005/006964 filed Apr. 8, 2005 which designates the United States, incorporated herein by reference, and which claims the benefit of priority from Japanese Patent Application No. 2004-115848, filed Apr. 9, 2004, incorporated herein by reference.

BACKGROUND OF THE INVENTION

1. Field of the Invention

The present invention relates to an insertion shape detecting probe, and more particularly to an insertion shape detecting probe that is either inserted into a treatment instrument insertion channel of the endoscope or secured to the insertion portion of the endoscope, to detect an insertion shape of an endoscope insertion portion.

2. Description of the Related Art

In recent years, an endoscope has been widely used in a medical field and an industrial field. Particularly, an endoscope with a flexible insertion portion allows examination of organs deep inside a body cavity with the insertion portion inserted into a curved body cavity without incising a patient body, and allows treatments and operations such as removal of polyps, if necessary, with a treatment instrument inserted into a treatment instrument insertion channel of the endoscope.

However, manipulative skills are required to smoothly insert an elongated insertion portion of an endoscope into the curved body cavity from, for example, the anus to examine inside a lower alimentary tract. This is because the operator is uncertain about where a distal end of the insertion portion is in the body cavity and what state the insertion portion is in.

The insertion state of the insertion portion of the endoscope may be determined from the location of the distal end of the insertion portion and the bending state of the insertion portion through X-ray radioscopy for detecting the shape of the endoscope in insertion, where the insertion portion includes an X-ray radiopaque portion. However, an endoscope shape detection apparatus using X-ray is large, so that such an apparatus which emits X-ray requires a large examination room.

Further, such an endoscope examination requires the operator to operate the endoscope as well as the X-ray apparatus, placing an additional burden on the operator. Hence, it is not necessarily preferable to detect the insertion state of the endoscope insertion portion by X-ray.

For this reason, conventionally, apparatuses described in the following, for example, as disclosed in JP-A No. 2003-047586 (KOKAI), are proposed. One conventional apparatus includes plural elements which transmit electromagnetic wave, ultrasonic wave, and the like, in an insertion portion of an endoscope; and an external detector which receives a signal transmitted from a transmitting element of the insertion portion, to display an insertion portion shape on a monitor of the detector during insertion of the insertion portion. Another conventional apparatus includes an insertion shape detecting probe which has a magnetic field detecting element, to display an insertion portion shape on a monitor of a detector during insertion of an insertion portion by inserting the insertion portion into a body cavity with the insertion shape detecting probe inserted into a treatment instrument insertion channel provided in an endoscope.

The insertion shape detecting probe that is disclosed in JP-A No. 2003-047586 (KOKAI) includes an elongated core wire that, plural inner sheaths, a connecting-and-securing unit, and an outer sheath. Plural shape detecting elements from which signal lines are extended are secured on the core wire at predetermined intervals. Each inner sheath is arranged at the proximal end portion side of each shape detecting element that is secured on the core wire, and the core wire and the signal lines run through the inner sheaths. The connecting-and-securing unit covers and integrally connects each shape detecting element and each inner sheath that is adjacent to each shape detecting element. The plural shape detecting elements that are integrated with the core wire and the plural inner sheaths are inserted inside the outer sheath. Then, the insertion shape detecting probe detects the endoscope insertion portion shape with high accuracy by inserting the insertion shape detecting probe into the treatment instrument insertion channel of the endoscope and arranging the insertion shape detecting probe therein.

Here, in the insertion shape detecting probe according to JP-A No. 2003-047586 (KOKAI), the plural shape detecting elements (coils) are secured on the elongated core wire with the predetermined intervals, the plural inner sheaths through which the core wire and the signal lines (lead lines) that are extended from each shape detecting element run are arranged at the proximal end portion side of each shape detecting element, and the connecting-and-securing unit covers and integrally connects each shape detecting element and each inner sheath that is adjacent thereto. Consequently, each shape detecting element, each inner sheath, and the signal lines are linearly arranged; therefore, improvement in assembliability and miniaturization of the insertion shape detecting probe is realized.

SUMMARY OF THE INVENTION

An insertion shape detecting probe according to the present invention includes plural shape detecting elements that is used to detect a position of an insertion portion for generating magnetic field or detecting magnetic field; plural signal lines that are connected to the plural shape detecting elements; plural supporting members that support the plural shape detecting elements; and plural inner sheaths into which the signal lines and the supporting members are inserted. The inner sheaths are each formed by a multiple-lumen tube that has a first lumen formed at a substantially central portion of each inner sheath and plural second lumens formed around an exterior periphery portion of the first lumen. The shape detecting elements and the inner sheaths are linearly arranged. The supporting members are elongated wire rods in which one portion thereof is arranged along exterior peripheries of the shape detecting elements in an axial direction and other portion thereof runs through the second lumens of the inner sheaths. The insertion shape detecting probe also includes an outer sheath into which the inner sheaths, the shape detecting elements, and at least one portion of the supporting members are inserted.

The above and other objects, features, advantages and technical and industrial significance of this invention will be better understood by reading the following detailed descrip-

BRIEF DESCRIPTION OF THE DRAWINGS

FIG. 11 is a longitudinal sectional view of a coil protecting member (connecting-and-securing member) in an axial direction of the insertion shape detecting probe;

FIG. 13 is a longitudinal sectional view of a coil protecting member (connecting-and-securing member) in the axial direction of the insertion shape detecting probe;

DETAILED DESCRIPTION OF THE PREFERRED EMBODIMENTS

The present invention will be explained below based on embodiments shown in drawings.

Figure 1:
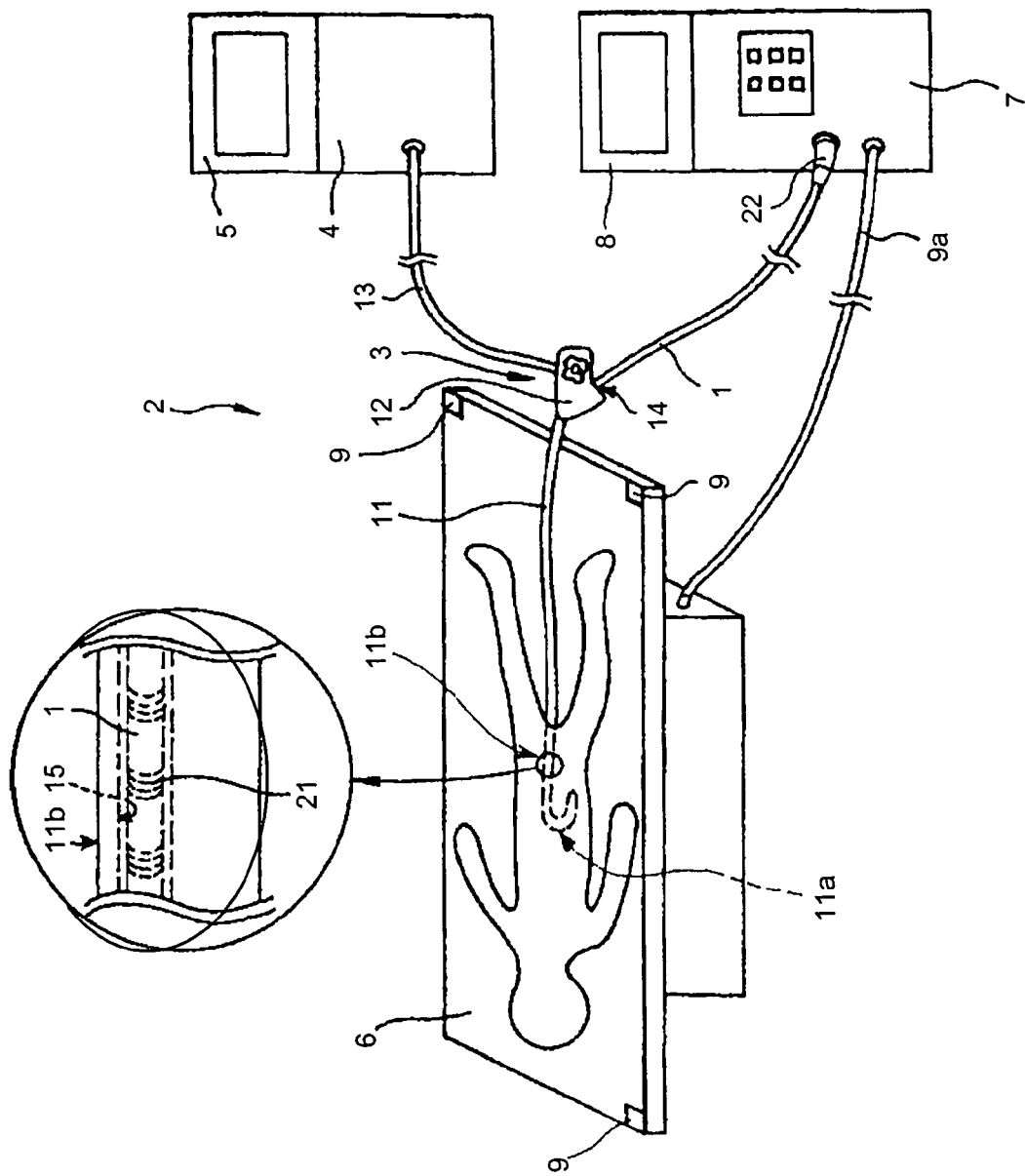
FIG. 1 is a system diagram showing a schematic configuration of an endoscope system to which an insertion shape detecting probe of a first embodiment of the present invention is applied.
Figure 2:
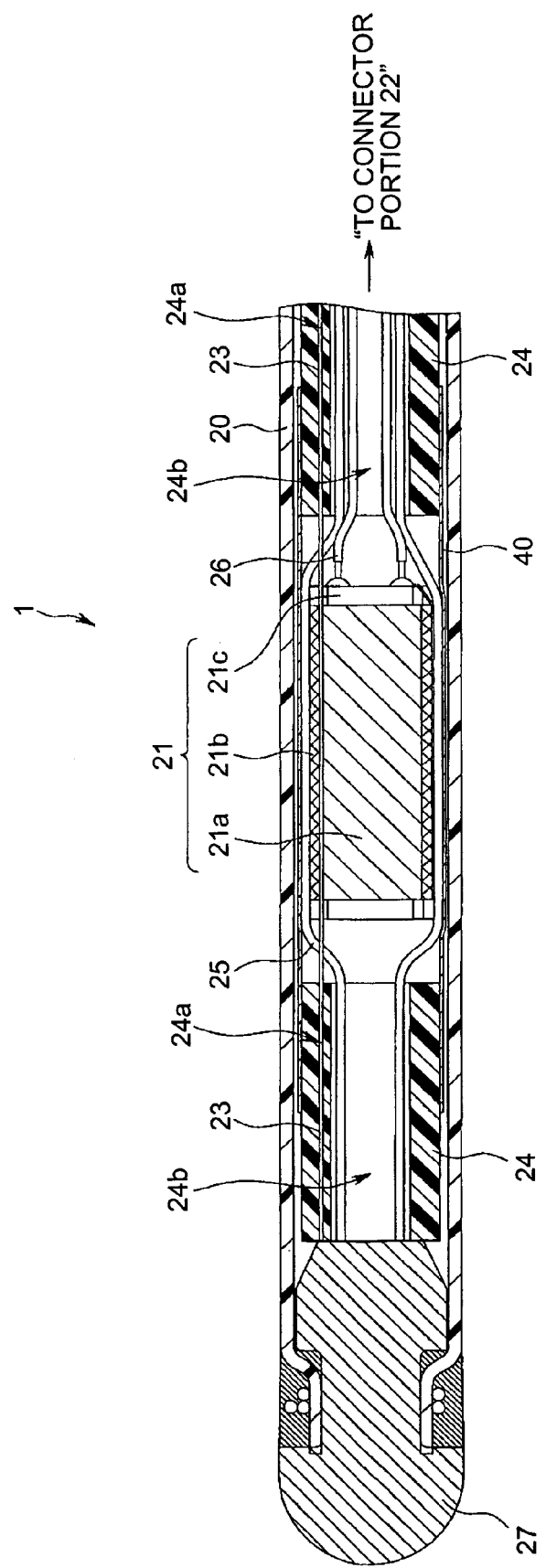
FIG. 2 is an enlarged sectional view of a major portion, showing a schematic configuration near a distal end portion, of internal components of the insertion shape detecting probe of FIG. 1.
Figure 3:
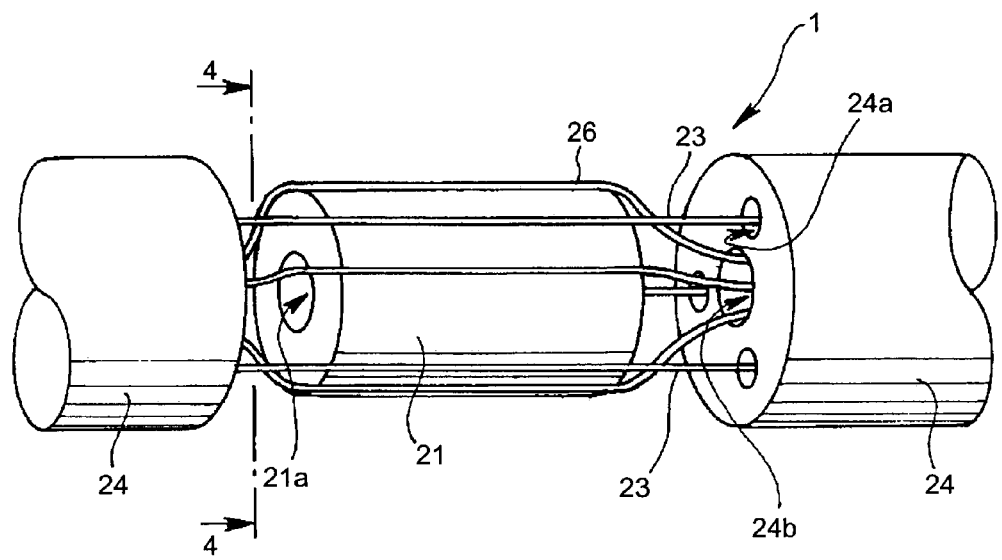
FIG. 3 is a schematic drawing showing one portion of interior members of the insertion shape detecting probe of FIG. 1.
Figure 4:
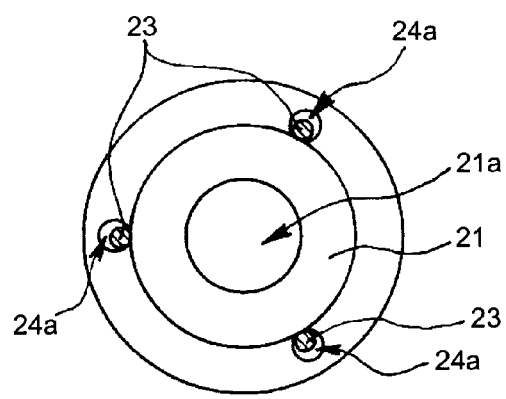
FIG. 4 is a sectional view taken along 4-4 line taken in the direction of arrow in FIG. 3.
Figure 5:
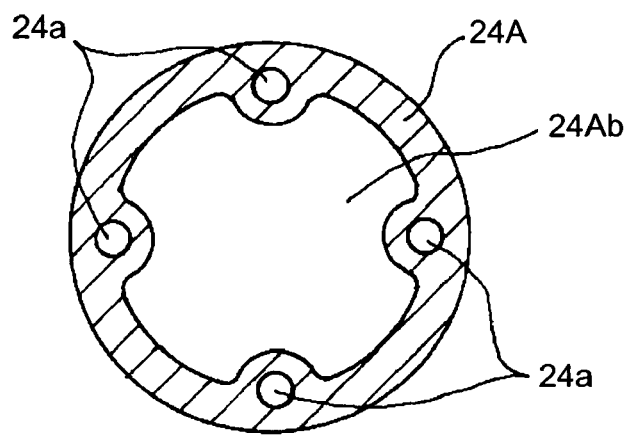
FIG. 5 is a sectional view showing a modification of a cross section of a multiple-lumen tube that is applied to the first embodiment of the present invention.
Figure 6:
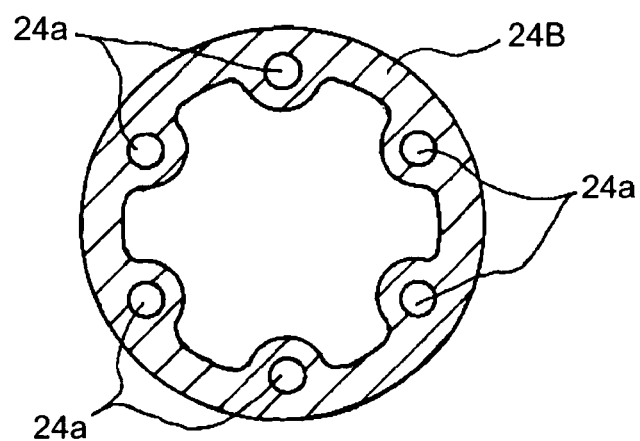
FIG. 6 is a sectional view showing a modification of the cross section of the multiple-lumen tube that is applied to the first embodiment of the present invention.

FIG. 1 is a system drawing showing a schematic configuration of an endoscope system to which an insertion shape detecting probe of a first embodiment of the present invention is applied. FIG. 2 is an enlarged sectional view of a major portion, showing a schematic configuration near a distal end portion, of internal components of the insertion shape detecting probe of the present embodiment. FIG. 3 is a schematic drawing showing one portion of interior members of the insertion shape detecting probe of the present embodiment. FIG. 4 is a sectional view taken along 4-4 line and taken in the direction of an arrow in FIG. 3. FIGS. 5 and 6 are sectional views showing modifications of cross sections of multiple-lumen tubes that are applied to the present embodiment.

As shown in FIG. 1, an endoscope system 2 to which an insertion shape detecting probe 1 of the present embodiment is applied includes an endoscope 3, a video processor 4, a monitor 5, an insertion shape detecting bed 6, an insertion shape detecting apparatus 7, and a monitor 8. The endoscope 3 is inserted into a body cavity and the like of a subject from, for example, the anus, and used to observe an observation region. The video processor 4 generates a video signal from an imaging signal acquired through imaging by the endoscope 3. The monitor 5 displays the image signal from the video processor 4 as an endoscope image. The insertion shape detecting bed 6 detects a magnetic field from the insertion shape detecting probe 1 while the subject lies down thereon. The insertion shape detecting apparatus 7 drives the insertion shape detecting probe 1 as well as outputs a video signal which is generated from a signal corresponding to the magnetic field that is detected by the insertion shape detecting bed 6 and which indicates an image of the insertion shape of the endoscope 3 inside the body cavity. The monitor 8 displays the insertion portion shape that is output from the insertion shape detecting apparatus 7.

The endoscope 3 includes an elongated insertion portion 11, a manipulator portion 12, and a universal cord 13. The insertion portion 11 has an insertion portion bendable portion 11a, which is arranged at a distal end side and bent with a small curvature radius, and an insertion portion flexible tube portion 11b, which is arranged at a proximal end side with respect to the insertion portion bendable portion 11a and bent with a comparatively large curvature radius, and the insertion portion 11 is inserted into the body cavity. The manipulator portion 12 is arranged at a proximal end side of the insertion portion 11, and the manipulator portion 12 serves also as a grip portion. The universal cord 13 is extended from a side portion of the manipulator portion 12 and connected to external devices such as the video processor 4.

The insertion shape detecting probe 1 is inserted into a treatment instrument insertion channel 15 from a treatment instrument insertion opening 14 that is provided on the manipulator portion 12 of the endoscope 3, and arranged therein. Plural source coils 21 and the like that are shape detecting elements for, for example, generating a magnetic field, are arranged in the insertion shape detecting probe 1 (see FIG. 2 for more details). Then, the insertion shape detecting probe 1 is connected to the insertion shape detecting apparatus 7 through a connector portion 22 provided at a proximal end portion of the insertion shape detecting probe 1.

Plural sense coils 9 that are magnetic field detecting elements for detecting magnetic field generated at the source coils 21 are arranged at the insertion shape detecting bed 6. The insertion shape detecting bed 6 and the insertion shape detecting apparatus 7 are connected to each other through a cable 9a. Consequently, detection signals of the sense coils 9 are transmitted to the insertion shape detecting apparatus 7 through the cable 9a.

The insertion shape detecting apparatus 7 has a source coil driving portion (not shown), a source coil position analyzing portion (not shown), an insertion shape image generating portion (not shown), and the like. The source coil driving portion drives the source coils 21. The source coil position analyzing portion analyzes three-dimensional position coordinates of the source coils 21 based on signals transmitted from the sense coils 9. The insertion shape image generating portion calculates three-dimensional shape of the insertion portion 11 from three-dimensional position coordinate information of the source coils 21, converts the calculated three-dimensional shape to two-dimensional coordinates that is able to be displayed on a monitor, and forms an image.

In the present embodiment, an example in which the plural shape detecting elements (source coils 21) for generating magnetic field are arranged in the insertion shape detecting probe 1 and the plural magnetic field detecting elements (sense coils 9) are arranged at the insertion shape detecting bed 6 is shown. However, the present invention is not limited thereto, and for example, the plural shape detecting elements (sense coils) for detecting magnetic field may be arranged in the insertion shape detecting probe 1 and the plural magnetic field generating elements (source coils) may be arranged at the insertion shape detecting bed 6.

Next, detailed configuration of the insertion shape detecting probe 1 is explained below.

As shown in FIGS. 2 to 4, the insertion shape detecting probe 1 includes an outer sheath 20 that forms an outer region, the plural source coils 21 (only one is shown in FIG. 2), inner sheaths 24, plural core wires 23, a connecting-and-securing member 40, a distal end piece 27, and the like. The source coils 21 have solid cores and have substantially cylindrical shapes. The inner sheaths 24 are arranged linearly with respect to the plural source coils 21 and formed by multiple-lumen tubes. The core wires 23 are formed by elongated wire rods that are coil supporting members, and the core wires 23 are each arranged in the plural lumens of the inner sheaths 24 as well as the core wires 23 are arranged as to run along exterior periphery faces of the plural source coils 21. The connecting-and-securing member 40 is formed by a thermally shrinkable tube and the like, and the connecting-and-securing member 40 covers and integrally connects each source coil 21 and a portion of each of the inner sheaths 24 that are adjacent to the source coil 21. The distal end piece 27 is provided at the most distal end portion of the outer sheath 20.

The source coils 21 and the inner sheaths 24 are alternately arranged as, the source coil 21 (the most distal end portion), the inner sheath 24, the source coil 21 (second from the most distal end portion), the inner sheath 24, the source coil 21 (third from the most distal end portion)..., in this order from a probe distal end side towards a proximal end portion, so that the source coils 21 and the inner sheaths 24 are arranged alternately.

As described above, the connecting-and-securing member 40 is arranged between each source coil 21 and each inner sheath 24 that is adjacent to each source coil 21. The connecting-and-securing member 40 is arranged so as to cover each source coil 21 as well as cover both end portions of the inner sheaths 24. Consequently, the plural sets of the source coil 21 and the inner sheaths 24 are integrally connected.

Two signal lines 26 that transmit driving signals from the source coil driving portion (not shown) of the insertion shape detecting apparatus 7 are connected to one end portion of each source coil 21. The signal lines 26 run through inside the inner sheath 24 that is arranged at a proximal end portion side of each source coil 21, and the signal lines 26 are extended towards a proximal end portion side while running along an exterior periphery face of each source coil 21 that is arranged at a proximal end portion side of each inner sheath 24 just mentioned. Here, each signal line 26 runs through inside the connecting-and-securing member 40.

In other words, after the signal lines 26 that are extended from each source coil 21 run through inside each inner sheath 24 at the proximal end portion side of each source coil 21, the signal lines 26 are arranged along the exterior periphery face of the source coil 21 adjacent to each inner sheath 24 as well as run through inside the connecting-and-securing member 40. Then, again, the signal lines 26 run through inside the next inner sheath 24. At last, all of the signal lines 26 are extended to the connector portion 22 at the proximal end portion side of the present insertion shape detecting probe 1.

Therefore, more signal lines 26 run through inside the inner sheath 24 that is arranged near the proximal end portion of the insertion shape detecting probe 1, and further, more signal lines 26 run along the exterior periphery face of the source coil 21 that is arranged near the proximal end portion of the insertion shape detecting probe 1.

The signal lines 26 are made from metals, which have good electrical conductivity, such as copper. Further, the signal lines 26 have good heat conductivity since metals such as copper has good heat conductivity.

Each source coil 21 has a core member 21a having a solid cylindrical shape, a winding wire 21b that is enamel wire and the like, and a substrate 21c having a substantially discoidal shape. The winding wire 21b is wound around an exterior periphery of the core member 21a, and the substrate 21c is arranged on an end face of the core member 21a.

Both end portions of the winding wire 21b and a pair of the signal lines 26 are electrically connected to the substrate 21c by soldering and the like. Consequently, the pair of the signal lines 26 is extended from one end face side of each source coils 21.

Each source coil 21, each inner sheath 24, and each signal line 26 that are configured as described hereinbefore run through inside the outer sheath 20 while being arranged linearly and being connected to each other.

As described above, the inner sheaths 24 are arranged linearly with respect to the plural source coils 21. Each inner sheath 24 is formed from a multiple-lumen tube having a first lumen 24b with a large diameter and plural second lumens 24a with small diameters (see FIG. 2). The first lumen 24b is formed at a substantially central portion of each inner sheath 24 as shown in FIGS. 3 and 4, and the second lumens 24a are formed around an outer periphery of the first lumen 24b equiangularly. Then, the signal lines 26 run through inside the first lumen 24b, and the core wires 23 run through the second lumens 24a.

Distal end portions of the core wires 23 are secured to the distal end piece 27 at the most distal end portion of the present insertion shape detecting probe 1. Then, the core wires 23 run through the second lumens 24a of the inner sheath 24 that is arranged the nearest to the distal end of the insertion shape detecting probe 1, are extended towards the proximal end portion of the insertion shape detecting probe 1 so as to run along the exterior periphery face of the source coil 21 at the proximal end portion side of the inner sheath 24, run through the second lumen 24a of the next inner sheath 24, repeat the configurations just mentioned, and are extended to the connector portion 22 of the proximal end portion of the present insertion shape detecting probe 1. Then, other end portions (proximal end portions) of the core wires 23 are secured with respect to a securing portion of the connector portion 22.

The insertion shape detecting probe 1 acquires flexibility and elasticity because of the core wire 23 arranged between the distal end portion and the proximal end portion of the present insertion shape detecting probe 1 as described above. Further, at the same time, the core wires 23 serve as coil supporting members that support to linearly arrange the source coils 21, since the core wires 23 are arranged so as to run along the exterior periphery faces of the source coils 21.

A metal member with rigidity, a shape memory metal with a linear shape memory, a metal member that has high heat conductivity such as, for example, silver, copper, or gold, a thin tube member that is formed from a resin member or an elastic member, superelastic wire rod, or the like is used as rod materials that form the core wires 23.

When the metal member is used as the materials of the core wires 23, short circuit is caused due to physical contact in which the core wires 23 directly touch the exterior peripheries of the source coils 21. In order to avoid the short circuit, surface treatment such as resin coating is performed on surfaces of the core wires 23. Consequently, the short circuit between the source coils 21 and the core wires 23 are avoided, and insulation state therebetween is secured.

In the present embodiment, three core wires 23 are provided by forming three second lumens 24a, through which the core wires 23 run, of the plural lumens of the inner sheaths 24, and the three core wires 23 support the source coils 21.

However, the configuration of the inner sheaths 24 is not limited thereto, and the inner sheaths 24 may have different configuration.

For example, by forming inner sheaths 24A or 24B in which the number of second lumens 24a is increased as shown in FIGS. 5 and 6, to increase the number of core wires 23, the flexibility and elasticity of the insertion shape detecting probe that uses the inner sheaths 24A or 24B may be adjusted at will.

Then, similarly, by properly selecting rigidity of the materials of the core wires 23, the flexibility and elasticity of the insertion shape detecting probe may also be adjusted at will.

Furthermore, thicker core wires 23 may be used by forming the inner sheaths 24 in which inner diameters of the second lumens 24a are thickened. Therefore, the flexibility and elasticity of the insertion shape detecting probe can be adjusted at will by selecting diameters of the core wires 23 to be used at will.

Similarly, by forming the inner sheaths 24 in which inner diameters of the first lumens 24b are thickened, the number of signal lines 26 and the like that run through the first lumens 24b can be increased so that the number of source coils 21 that are able to be arranged with a constant interval may be increased. Consequently, the increase in the number of signal lines 26 and the like may contribute to improvement of shape detection accuracy, and at the same time, an entire length of the insertion shape detecting probe may be elongated.

Further, rigidity of the inner sheaths 24 may be changed by changing tube wall thicknesses; therefore, an insertion shape detecting probe, which is formed by using the inner sheaths 24 just mentioned, with different rigidity may easily be formed.

In a predetermined area extended from a predetermined region at the distal end side of the insertion shape detecting probe 1 towards the proximal end side, plural thermally radiating members 25 are arranged along the exterior peripheries of the source coils 21 in regions of the source coils 21, and inserted into the first lumens 24b at regions of the inner sheaths 24. Wire rods having good heat conductivity such as copper are used as materials of the thermally radiating members 25. Therefore, thermal radiation effect is obtained by having portions of the thermally radiating members 25 touch the exterior peripheries of the source coils 21.

As for the thermally radiating members 25, the surface treatment such as the resin coating is performed on surfaces of the thermally radiating members 25 in order to avoid short circuit caused by having the thermally radiating members 25 directly touch the exterior peripheries of the source coils 21. Consequently, insulation state between the thermally radiating members 25 and the source coils 21 is achieved. The thermally radiating members 25 are only shown in FIG. 2, and not shown in FIGS. 1, 3, and 4 in order to avoid complexity in the drawings.

The connecting-and-securing member 40 that is formed from a thermally shrinkable tube and the like, is arranged between each source coil 21 and the inner sheaths 24 that are adjacent to each source coil 21, as described above.

Figure 7:
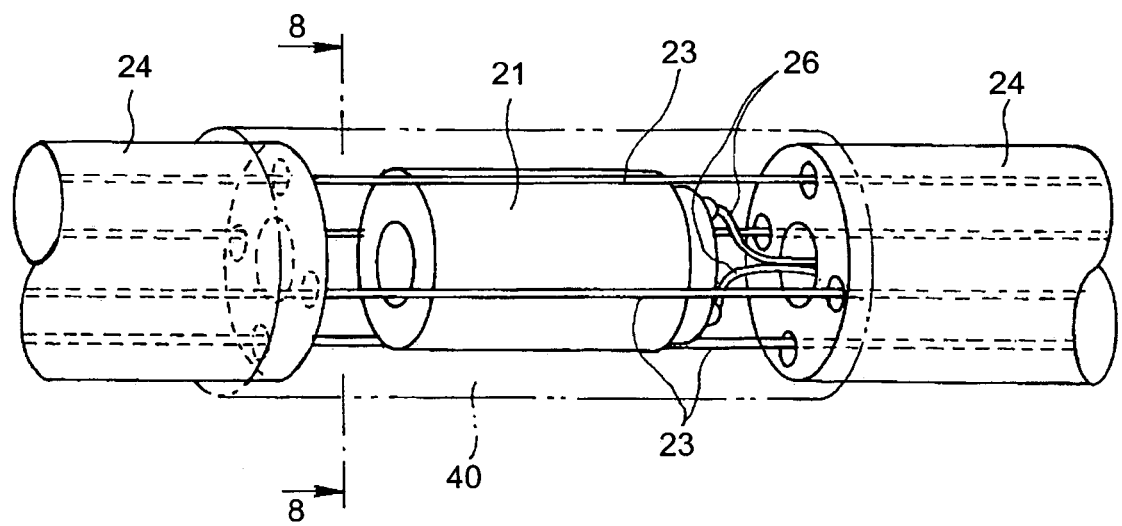
FIG. 7 is a schematic drawing showing a coil protecting member in the insertion shape detecting probe of FIG. 1.
Figure 8:
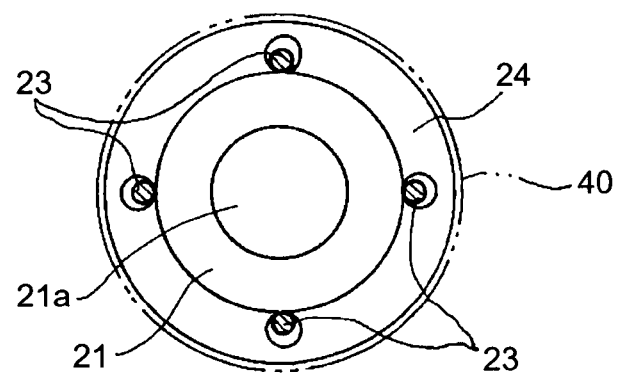
FIG. 8 is a sectional view taken along 8-8 line taken in the direction of arrow of FIG. 7.

FIG. 7 is a schematic drawing showing a coil protecting member in the insertion shape detecting probe of the present embodiment. FIG. 8 is a sectional view taken along 8-8 line in the direction of an arrow of FIG. 7.

As shown in FIG. 7, the connecting-and-securing member 40 functions as a connecting member that integrally connects each source coil 21 and the inner sheaths 24 as well as functions as a coil protecting member that protects a region including the exterior periphery of the source coils 21 by covering the exterior periphery of each source coil 21 and one portion of each end portion of two inner sheaths 24 that are adjacent to each source coil 21.

A configuration described below, for example, is applied to a configuration of the connecting-and-securing member 40.

Figure 9:
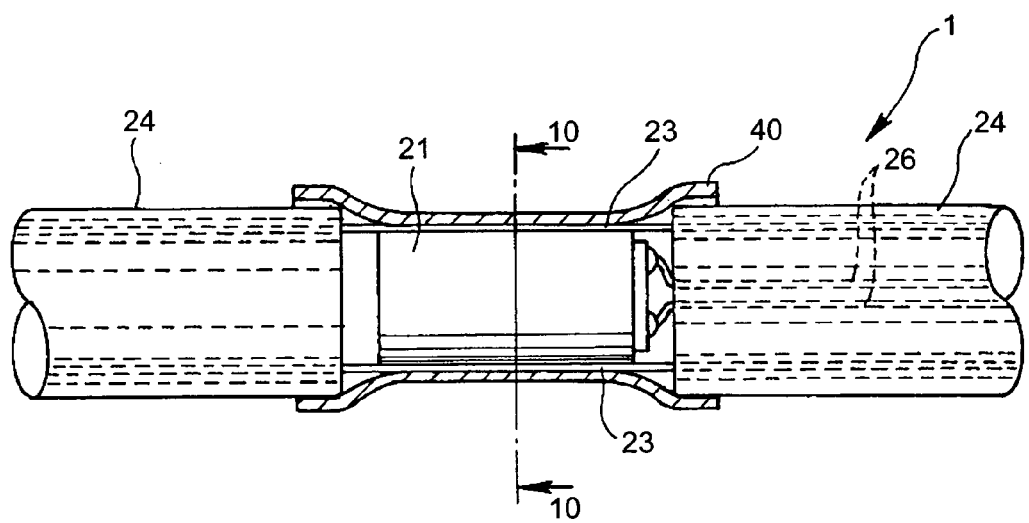
FIG. 9 is a longitudinal sectional view in an axial direction of the coil protecting member (connecting-and-securing member) in the insertion shape detecting probe of FIG. 1.
Figure 10:
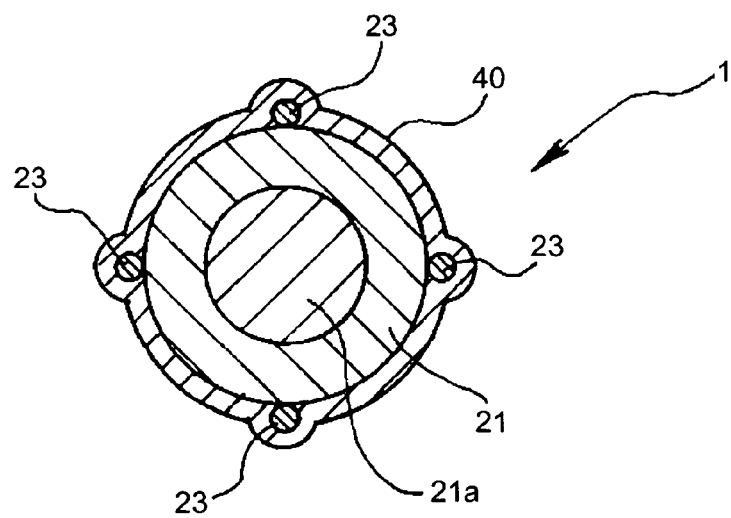
FIG. 10 is a sectional view taken along 10-10 line of FIG. 9.

FIGS. 9 and 10 are drawings showing one example of the coil protecting member (connecting-and-securing member) in the insertion shape detecting probe of the present embodiment. FIG. 9 is a longitudinal sectional view in an axial direction of the coil protecting member (connecting-and-securing member). FIG. 10 is a sectional view taken along 10-10 line of FIG. 9.

The thermally shrinkable tube is applied for the connecting-and-securing member 40 that is the coil protecting member in the insertion shape detecting probe 1 of the present embodiment. The connecting-and-securing member 40 covers the exterior periphery of each source coil 21 to protect each source coil 21 since the connecting-and-securing member 40 is arranged so as to adhere to the exterior periphery face of each source coil 21 as shown in the drawings.

Here, the core wires 23 touch and hold the exterior periphery of each source coil 21. Therefore, the connecting-and-securing member 40 is arranged so as to adhere to the core wires 23 from the exterior peripheries thereof, so as to cover and protect each of the core wires 23. Consequently, at positions where the core wires 23 are arranged as shown in FIG. 10, protruding portions, which point outward, are formed on the exterior periphery of each source coil 21.

Further, though not shown in FIG. 10, signal lines 26 are arranged on the exterior periphery of each source coil 21. As similar to the core wires 23, the signal lines 26 are also adhered and secured to the exterior periphery of each source coil 21 by the connecting-and-securing member 40, so as to be covered and protected by the connecting-and-securing member 40 from the exterior peripheries of the signal lines 26.

Then, both end portions of the connecting-and-securing member 40 cover and protect one portion of each end portion of the inner sheaths 24 that are adjacent to each source coil 21. Consequently, each source coil 21 and both inner sheaths 24 that are adjacent to each source coil 21 are integrally connected.

As described above, according to the aforementioned first embodiment, each inner sheath 24 that is formed from the multiple-lumen tube is applied to the insertion shape detecting probe, and the multiple-lumen tube is configured so that the core wires 23 that support the source coils 21 and the signal lines 26 that are extended from the source coils 21 run through the plural lumens formed in the inner sheaths 24. Therefore, volume of the core 21a can be increased compared to a core of a conventional type in which the core wire runs through centers of cores of source coils. Consequently, miniaturization of the source coils 21 can be realized, while maintaining output performance. Further, the source coils 21 can easily be miniaturized, so that the miniaturization can contribute to the miniaturization of the insertion shape detecting probe 1 to which the source coils just mentioned are applied.

Further, plural core wires 23 that are the coil supporting members supporting the source coils 21 are used. Hence, by properly selecting number, thickness, and material of the core wires 23, the flexibility and elasticity of the insertion shape detecting probe 1 that uses the core wires 23 may be adjusted at will. Therefore, plural types of the insertion shape detecting probe 1 having desired flexibility and elasticity may extremely easily be realized.

The thermally shrinkable tube is used as the connecting-and-securing member 40 that is the coil protecting member connecting each source coil 21 and the inner sheaths 24 that are adjacent to each source coil 21 as well as covering and protecting the exterior faces of each source coil 21. Hence, the thermally shrinkable tube can protect the exterior periphery surface of each source coil 21, can secure the signal lines 26 that are arranged along the exterior face of each source coil 21, and can secure each source coil 21 with respect to the core wires 23.

Furthermore, each inner sheath 24 in the insertion shape detecting probe 1 of the present embodiment uses the multiple-lumen tube. The first lumen 24b of the multiple-lumen tube may have a shape as shown in FIGS. 5 and 6. As described above, by changing the shape of the first lumen 24b, plural types of the insertion shape detecting probe 1 having flexibility and elasticity of the insertion shape detecting probe 1 to which the first lumen 24b just mentioned is applied can extremely easily be realized.

In the present embodiment, the connecting-and-securing member 40 that is the coil protecting member is formed with the thermally shrinkable tube; however, the connecting-and-securing member 40 may be formed by material that is more flexible than the thermally shrinkable tube, such as elastic member, i.e., rubber tube, having thin wall. Then, when the insertion shape detecting probe 1 is used and bent, an effect in which the insertion shape detecting probe is more flexibly bent can be obtained.

Further, a configuration described below, for example, may be used as a configuration of the connecting-and-securing member 40, other than aforementioned thermally shrinkable tube and elastic member.

Figure 11:
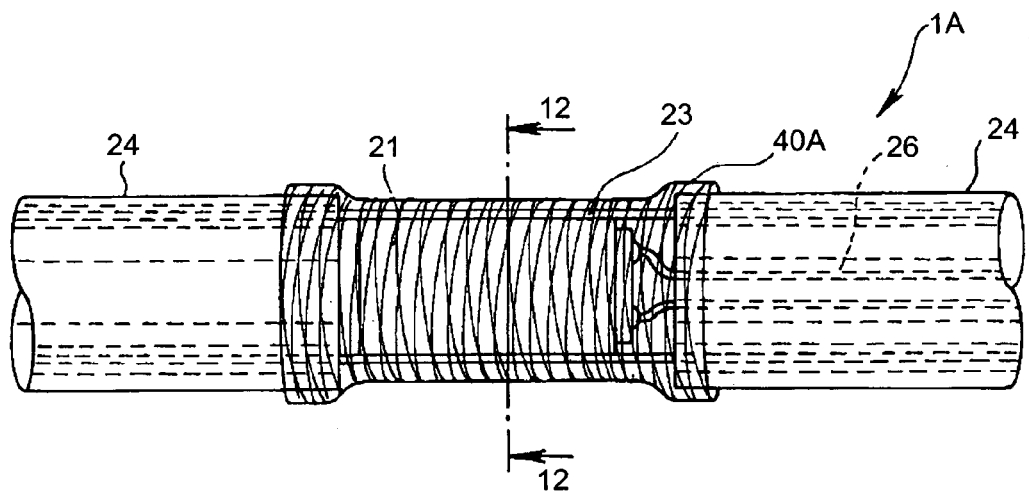
FIG. 11 shows a first modification of the coil protecting member (connecting-and-securing member) in the insertion shape detecting probe of FIG. 1.
Figure 12:
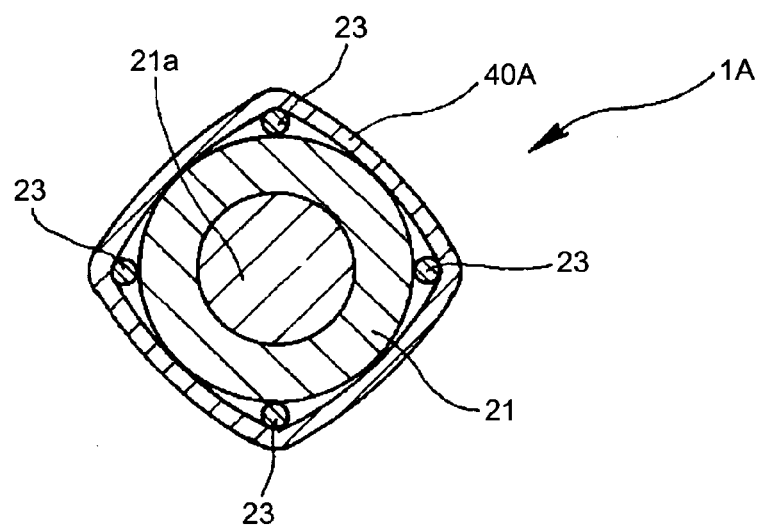
FIG. 12 is a sectional view taken along 12-12 line of FIG. 11.

FIGS. 11 and 12 are drawings showing a first modification of the coil protecting member (connecting-and-securing member) in an insertion shape detecting probe 1A of the present embodiment. FIG. 11 is a longitudinal sectional view of a coil protecting member (connecting and securing member) in an axial direction of the insertion shape detecting probe. FIG. 12 is a sectional view taken along 12-12 line of FIG. 11.

A stringlike fiber member such as Kevlar® having extremely low degree of extensibility and high strength is used as a connecting-and-securing member 40A that is the coil protecting member of the present modification. In the present modification, the fiber member is wound around each source coil 21 in a reticular pattern so as to cover and protect the exterior periphery of each source coil 21 and a region of one portion of each end portion of the two inner sheaths 24 that are adjacent to each source coil 21 as shown in FIG. 11. Here, the fiber member is wound around the exterior peripheries of the core wires 23 that support the source coils 21. Therefore, the core wires 23 serve as a guide when the fiber member is wound around each source coil 21. Material having flexibility such as rubber like material or nylon string may be used as the fiber member. In other words, the fiber member is better selected depending on desired elasticity.

As described above, the fiber member at last forms the connecting-and-securing member 40A as shown in FIG. 11. Here, since the connecting-and-securing member 40A is arranged to adhere to the core wires 23 so as to cover and protect even the exterior periphery of the core wires 23, protruding portions that point outward are formed at a region of the core wires 23 on the exterior peripheries of the source coils 21 as shown in FIG. 12.

In the aforementioned first modification, the connecting-and-securing member 40A is formed by winding the fiber member in reticular shape. However, the present invention is not limited thereto, and the connecting-and-securing member 40A may be formed with various winding styles.

Figure 13:
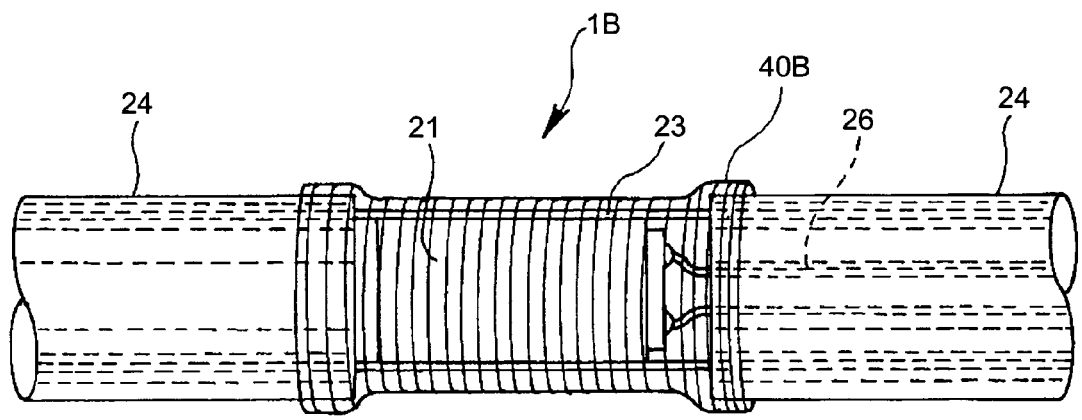
FIG. 13 shows a second modification of the coil protecting member (connecting-and-securing member) in the insertion shape detecting probe of FIG. 1.

For example, FIG. 13 shows a second modification of the coil protecting member (connecting-and-securing member) in an insertion shape detecting probe 1B of the present embodiment, and FIG. 13 is a longitudinal sectional view of a coil protecting member (connecting-and-securing member) in the axial direction of the insertion shape detecting probe 1B.

The second modification is an example in which the coil protecting member is formed by winding the fiber member around the exterior periphery and the like of each source coil 21, as similar to the aforementioned first modification. However, the second modification differs from the aforementioned first modification, in which the fiber member is wound in reticular shape, since a connecting-and-securing member 40B is formed by sequentially winding the fiber member around the exterior periphery of each source coil 21. Other configurations are the same as the configuration of the aforementioned first modification.

As shown in the aforementioned first and the second modifications, when the connecting-and-securing members (40A, 40B) are formed by winding the fiber member around the exterior periphery of each source coil 21 and the like, the flexibility and elasticity of the insertion shape detecting probes (1A, 1B) may be adjusted to desired state by adjusting strength of the winding or by forming the connecting-and-securing member with different winding style or with different material of the fiber member.

In the aforementioned first embodiment and the modifications thereof, the short circuit caused due to the physical contact between the core wires 23 and the source coils 21 is avoided by performing the surface treatment such as, for example, the resin coating on the surface of the core wires 23, so that the insulation state therebetween is obtained.

A configuration for obtaining the insulation state between the core wires 23 and the source coils 21 is not limited to the aforementioned configuration, and for example, a configuration that is shown hereinafter may be used.

Figure 14:
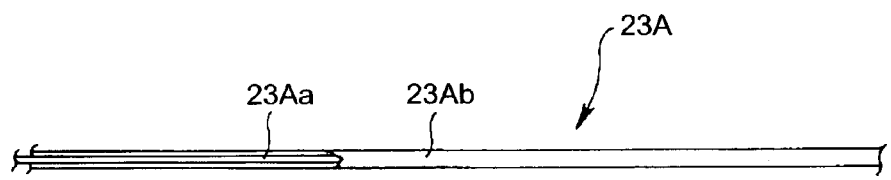
FIG. 14 is a schematic drawing illustrating a modification of a coil supporting member (core wire) in the insertion shape detecting probe of FIG. 1.

For example, FIG. 14 is a schematic drawing illustrating a modification of a coil supporting member (core wire) in the insertion portion detecting probe of the aforementioned first embodiment. In FIG. 14, one portion of the coil supporting member (core wire) is torn to show an interior configuration thereof.

Core wires 23A in the present modification are formed from wire rods 23Aa that are formed by metal members and the like and thin wall tubes 23Ab that cover exterior surfaces of the wire rods 23Aa. Consequently, the wire rods 23Aa are insulated with respect to outside.

The core wires 23A are applied to the insertion shape detecting probe 1 of the aforementioned first embodiment. The core wires 23A are arranged so as to run through the second lumens 24a at the regions of the inner sheaths 24 and to run along the exterior peripheries of the source coils 21 at the regions of the source coils 21. Here, the core wires 23A and the exterior peripheries of the source coils 21 are in contact with each other.

However, the wire rods 23Aa inside the core wires 23A are insulated from the source coils 21 by the thin wall tubes 23Ab. Therefore, the short circuit caused therebetween is prevented since the insulation state is obtained even if the core wires 23A and the exterior periphery face of the source coils 21 are in physical contact with each other.

In the aforementioned first embodiment and the modification thereof, the plural thermally radiating members 25 are arranged in a predetermined area extending from a predetermined region at the distal end side of the insertion shape detecting probe towards the proximal end side in order to prevent increase in surface temperature of the source coils 21 at the driving of the insertion shape detecting probes (1, 1A, 1B) as mentioned later. Thermal radiation effect is acquired by having one portion of the thermally radiating members 25 in contact with the exterior peripheries of the source coils 21 (see FIG. 2. Not shown in FIG. 1 and FIGS. 3 to 13).

However, a configuration described later may be considered instead of the thermally radiating members 25, to deal with the increase in the surface temperature of the source coils 21.

Figure 15:
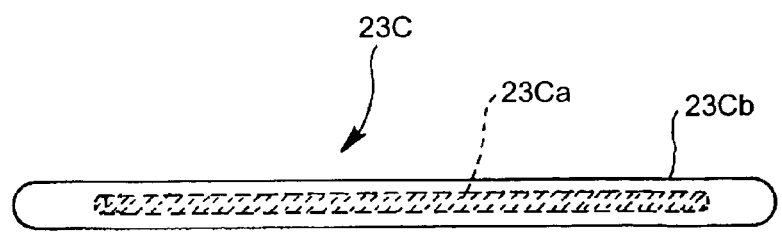
FIG. 15 is an enlarged view of a major portion showing a portion of an interior configuration of an insertion shape detecting probe of a second embodiment of the present invention.
Figure 16:
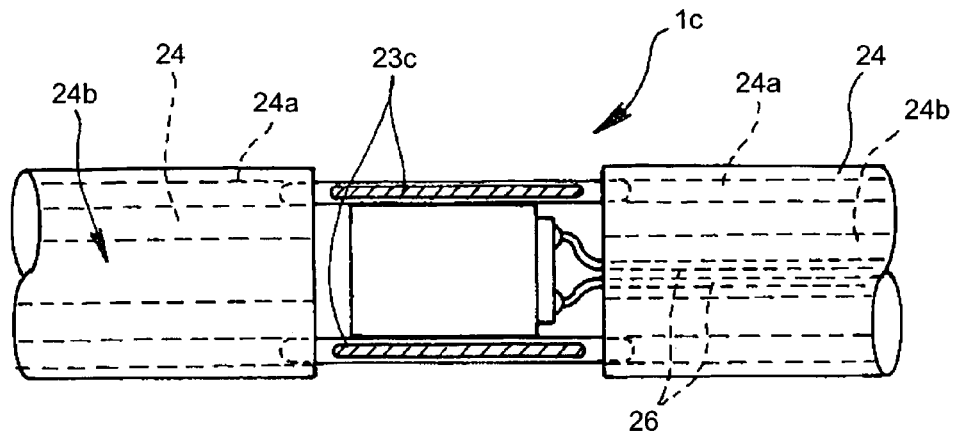
FIG. 16 is an enlarged view mainly showing a core wire in the insertion shape detecting probe of FIG. 15.

FIGS. 15 and 16 are drawings showing a second embodiment of the present invention. FIG. 15 is an enlarged view of a major portion showing an enlarged portion of an interior configuration of an insertion shape detecting probe of the present embodiment. FIG. 16 is an enlarged view mainly showing a core wire in the present insertion shape detecting probe.

Basic configurations of an insertion shape detecting probe 1C of the present embodiment is substantially the same as the configurations of the insertion shape detecting probe 1 of the aforementioned first embodiment. The insertion shape detecting probe IC of the present embodiment differs from the aforementioned first embodiment since, in the present embodiment, core wires 23C are used as the thermally radiating members, and the thermally radiating members 25 in the insertion portion detecting probe 1 of the aforementioned first embodiment are not provided. Therefore, the same letters and numerals are affixed for configurations that are similar to the configurations of the aforementioned first embodiment, and the explanations thereof are not to be repeated and only the member that differs from the aforementioned member is explained.

The core wires 23C in the insertion shape detecting probe 1C of the present embodiment are arranged at a region between the two inner sheaths 24 between which each source coil 21 is sandwiched, as shown in FIG. 16. Here, one portion of both ends of the core wires 23C are arranged in the second lumens 24a of each inner sheath 24. Then, a region at a middle of the core wires 23C touches the exterior periphery of each source coil 21, and supports each source coil 21.

In other words, in the present embodiment, plural short core wires 23C linearly connect inner sheaths 24 to each other as well as each core wire 23C supports each of the plural source coils 21.

The core wires 23C are formed so as to seal cooling mediums 23Ca inside thin tubes 23Cb, as shown in FIG. 15. Then, as described above, the core wires 23C touch the exterior periphery face of each source coil 21, and support each source coil 21. Here, the increase in the surface temperature of the source coils 21 is prevented by an effect of the cooling mediums 23Ca inside the core wires 23C. Other configurations are the same as the aforementioned configuration of the first embodiment.

As explained above, in the aforementioned second embodiment, a few configuration such as the thermally radiating members 25 are not provided, the source coils 21 are supported, and the increase in the surface temperature of the source coils 21 is surely prevented.

The flexibility and elasticity of the insertion shape detecting probe 1C may be adjusted by adjusting a length of a region of the core wires 23 that are to be arranged inside the second lumens 24a.

Next, the insertion shape detecting probe of the third embodiment of the present invention is explained below.

Figure 17:
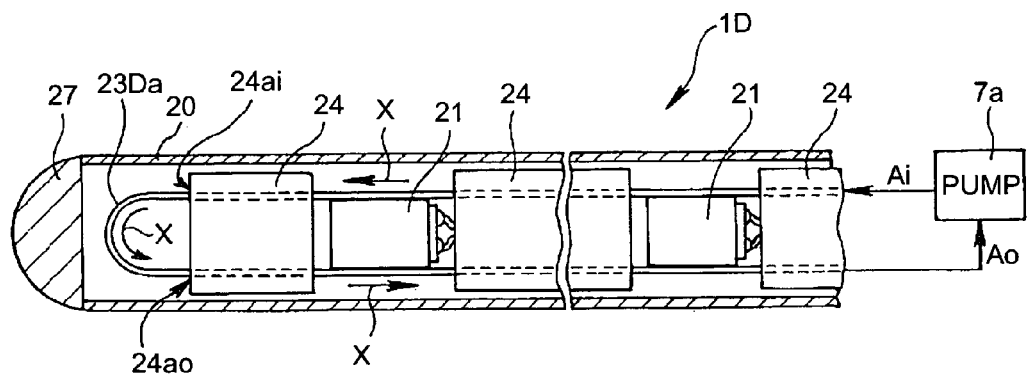
FIG. 17 is an enlarged sectional view of a major portion schematically showing an interior configuration of a region nearby a distal end portion of an insertion shape detecting probe of a third embodiment of the present invention.
Figure 18:
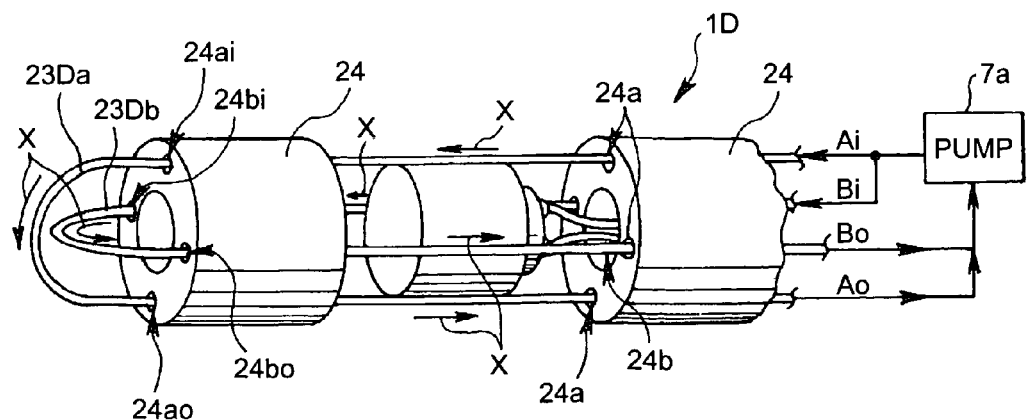
FIG. 18 is an enlarged view of a major portion schematically showing one portion of the interior member of FIG. 17.

FIGS. 17 and 18 are drawings showing configurations near a distal end portion in an insertion shape detecting probe of a third embodiment of the present invention. FIG. 17 is an enlarged sectional view of a major portion schematically, showing an interior configuration of a region near a distal end portion of the present insertion shape detecting probe. Further, FIG. 18 corresponds to FIG. 17, and FIG. 18 is an enlarged view of a major portion schematically showing one portion of the interior member of the present embodiment.

Basic configurations of an insertion shape detecting probe 1D of the present embodiment is substantially the same as the configuration of the insertion shape detecting probe 1 of the aforementioned-first embodiment. In the insertion shape detecting probe 1D of the present embodiment, hollow core wires 23Da and 23Db are arranged instead of the core wires 23C in the aforementioned first embodiment, and the core wires 23Da and 23Db may also be used as the thermally radiating members. The thermally radiating members 25 in the insertion shape detecting probe 1 of the aforementioned first embodiment are not provided in the present embodiment. Therefore, the same letters and numerals are affixed for configurations that are the same as the configurations of the aforementioned first embodiment, the explanations thereof are not to be repeated, and the members of the present embodiment that are different from the first embodiment are explained hereinafter.

In the insertion shape detecting probe 1D of the present embodiment, the two core wires 23Da and 23Db are formed by thin hollow duct members that are connected in a loop shape near the probe distal end portion, as shown in FIG. 18 (FIG. 17 only shows one of the core wires).

Proximal end portions of the pair of the core wires 23Da and 23Db are extended to a pump 7a that is provided inside the insertion shape detecting apparatus 7 (see FIG. 1) through the connector portion 22 (see FIG. 1) at a proximal end portion side of the insertion shape detecting probe 1D, and connected to the pump 7a.

In the middle of the core wires 23Da and 23Db inside the insertion shape detecting probe 1D, the core wires 23Da and 23Db are arranged as to run through the second lumens 24a at the regions of the inner sheaths 24 and to run along the exterior peripheries of the source coils 21 at the regions of the source coils 21.

Then, each of the core wires 23Da and 23Db is formed so as to form a connected loop shape at the distal end region of the insertion shape detecting probe 1D.

In other words, the core wire 23Da of the two core wires 23Da and 23Db is extended from the pump 7a, runs linearly through the second lumen 24a of the inner sheath 24 from the letter Ai at the probe proximal end portion side, arranged along the exterior periphery of the source coil 21, runs through the second lumen 24a of the next inner sheath 24, and arranged in this manner from here onward. Then, after the core wire 23Da is extended from the second lumen 24ai of the inner sheath 24 at the most distal end portion of the probe, the core wire 23Da is formed in the loop shape and runs through the second lumen 24ao of the same inner sheath 24. Then, the core wire 23Da is extended to the letter Ao at the proximal end portion side of the same probe, and connected to the pump 7a.

Similarly, the core wire 23Db is extended from the pump 7a, linearly arranged from the letter Bi at the probe proximal end portion side, extended from the first lumen 24bi of the inner sheath 24 at the most distal end portion of the probe, and formed in the loop shape. Then, after the core wire 23Db runs through the first lumen 24bo of the same inner sheath 24, the core wire 23Db is extended to the letter Bo at the proximal end portion side of the same probe, and connected to the pump 7a.

The pump 7a is arranged so as to circulate the cooling medium inside the core wires 23Da and 23Db. The pump 7a is drive-controlled by the aforementioned insertion shape detecting apparatus 7 (see FIG. 1). When the pump 7a is driven by the insertion shape detecting apparatus 7, the cooling medium inside the pump 7a flows into an arrow X direction from the letters Ai and Bi at the proximal end portion side of the core wires 23Da and 23Db that run through inside the insertion shape detecting probe 1D. Then, the cooling medium runs through the loop shape portion at the probe distal end portion, runs again towards the proximal end portion side, and runs to the pump 7a from the letters Ao and Bo.

The insertion shape detecting apparatus 7 can detect condition of the surface temperature of the source coils 21 by detecting the temperature and the like of the cooling medium that runs back to the pump 7a. Then, the insertion shape detecting apparatus 7 drive-controls the pump 7a based on the result just mentioned, and controls, for example, flow rate and pressure of the cooling medium.

As described above, the increase in the surface temperature of the source coils 21 is prevented by the effect of the cooling medium that runs through inside the core wires 23Da and 23Db. Other configurations are the same as the configurations of the aforementioned first embodiment.

According to the aforementioned third embodiment that has the configurations described hereinbefore, the thermally radiating members 25 in the aforementioned first embodiment and the like are unnecessary as similar to the aforementioned second embodiment, the source coils 21 are supported, and the increase in the surface temperature of the source coils 21 is surely prevented.

In the aforementioned embodiments and the modifications thereof, the core members of the source coils 21 are solid. However, the present invention is not limited thereto, even when the core member is hollow, the probe may be thinned down. When the hollow source coils 21 are compared to the solid source coils 21 while having number of winding the same, the outside diameter of the solid source coils 21 can be decreased so that an effect in which the probe is further miniaturized can be obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion shape detecting probe, comprising:
    plural shape detecting elements that is used to detect a position of an insertion portion for generating magnetic field or detecting magnetic field;
    plural signal lines that are connected to the plural shape detecting elements;
    plural supporting members that support the plural shape detecting elements;
    plural inner sheaths into which the signal lines and the supporting members are inserted, the inner sheaths being each formed by a multiple-lumen tube that has a first lumen formed at a substantially central portion of each inner sheath and plural second lumens formed around an exterior periphery portion of the first lumen, the shape detecting elements and the inner sheaths being linearly arranged, the supporting members being elongated wire rods in which one portion thereof is arranged along exterior peripheries of the shape detecting elements in an axial direction and other portion thereof runs through the second lumens of the inner sheaths; and
    an outer sheath into which the inner sheaths, the shape detecting elements, and at least one portion of the supporting members are inserted.

2. The insertion shape detecting probe according to claim 1, wherein
    the supporting members is configured to support the shape detecting elements and maintain linearity so that each supporting member touches the shape detecting elements at the exterior peripheries of the shape detecting elements.

3. The insertion shape detecting probe according to claim 1, wherein
    the wire rods of the supporting members are formed from metal members surfaces of which are resin coated and which have heat conductivity.

4. The insertion shape detecting probe according to claim 1, wherein
    the supporting members are formed from shape memory metals with linear shape memory.

5. The insertion shape detecting probe according to claim 1, wherein
    the supporting members include wire rods that are made from metal members having heat conductivity, and thin wall tubes that cover exterior surfaces of the wire rods.

6. The insertion shape detecting probe according to claim 1, wherein
    the supporting members are formed from thin tubes that are made from resin members or elastic members.

7. The insertion shape detecting probe according to claim 1, wherein
the supporting members are thin tubes inside which cooling mediums are sealed.

8. The insertion shape detecting probe according to claim 1, wherein
the supporting members are formed from thin hollow duct members that are connected in loop shapes at a probe distal end portion so that a cooling medium runs through inside the supporting members.

9. The insertion shape detecting probe according to claim 1, further comprising:
a protection member that is provided between each shape detecting element and inner sheaths that are adjacent to the shape detecting element to connect each shape detecting element to the inner sheaths that are adjacent to the shape detecting element as well as to protect an exterior periphery face of the shape detecting element.

10. The insertion shape detecting probe according to claim 9, wherein
the protection member is formed from a thermally shrinkable tube.

11. The insertion shape detecting probe according to claim 9, wherein
the protection member is formed from an elastic member with a thin wall.

12. The insertion shape detecting probe according to claim 9, wherein
the protection member is formed from a fiber member wound.

13. The insertion shape detecting probe according to claim 1, wherein
the plural shape detecting elements have cores, the cores having solid cylindrical shapes.

* * * * *